(12) United States Patent
Morken et al.

(10) Patent No.: US 6,442,234 B1
(45) Date of Patent: Aug. 27, 2002

(54) X-RAY INSPECTION OF BALL CONTACTS AND INTERNAL VIAS

(75) Inventors: David B. Morken, San Jose; Edward S. Alcid, Sunnyvale, both of CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/677,845

(22) Filed: Oct. 3, 2000

(51) Int. Cl.[7] .............................................. G01N 23/02
(52) U.S. Cl. ........................................ 378/58; 438/16
(58) Field of Search ............................ 378/58, 41, 51; 438/16

(56) References Cited

U.S. PATENT DOCUMENTS

| | | | | |
|---|---|---|---|---|
| 4,872,187 A | * | 10/1989 | Nakahata et al. | 378/4 |
| RE35,423 E | * | 1/1997 | Adams et al. | 378/58 |
| 6,118,843 A | * | 9/2000 | Jang et al. | 378/41 |
| 6,151,380 A | * | 11/2000 | Zweig et al. | 378/58 |
| 6,194,720 B1 | * | 2/2001 | Li et al. | 250/311 |
| 6,272,204 B1 | * | 8/2001 | Amtower et al. | 378/63 |

* cited by examiner

*Primary Examiner*—Robert H. Kim
*Assistant Examiner*—Glen Kao

(57) ABSTRACT

A method for performing inspection of raised electrical contacts, such as BGA and flip-chip-type contacts, and associated underlying vias. An electrical or electronic device or component having a major surface is provided including an array of closely spaced apart BGA flip-chip-type raised contacts with respective underlying vias. An area-of-interest (AOI), including at least one BGA or flip-chip-type contact/via structure is selected. The row containing the AOI is isolated, by computed tomography imaging, via electrical testing, or by removal, for example, from the electrical or electronic device or component. The AOI is mounted on an X-ray transparent substrate; and X-ray transmission imaging of the AOI is performed to inspect the at least one BGA or flip-chip-type contact/via structure for the presence of misalignments, voids, and delaminations.

12 Claims, 5 Drawing Sheets

X-RAY INSPECTION OF BALL CONTACTS AND INTERNAL VIAS

RELATED APPLICATIONS

This application contains subject matter similar to that disclosed in U.S. patent application Ser. No. 09/661,038, filed on Sep. 13, 2000.

FIELD OF THE INVENTION

The present invention relates to a method for performing inspection and analysis of electrical contacts and associated vias of electrical devices. More particularly, the present invention pertains to an improved method of inspection using X-ray analysis of flip-chip connection and/or ball grid contact arrays ("BGA") and their associated internal vias, such as are utilized in semiconductor integrated circuit ("IC") devices and circuit boards therefor, for determination of offset or misalignment, voids, and layer separation (i.e., delamination).

BACKGROUND OF THE INVENTION

An increasingly important aspect of semiconductor IC manufacturing technology is mounting of the semiconductor IC chip or die to an appropriate substrate. Frequently, this requires providing the chip or die with as many input/output ("I/O") terminals as is possible. As a consequence of the requirement for a large number of terminals to be formed on a limited amount of chip or die surface, so called "flip-chip" structures and bonding techniques have been developed in order to provide high a real density interconnections between the IC chip or die and the substrate.

According to flip-chip methodology, the IC chip or die is mounted via direct bonding to a substrate, e.g., an integrated circuit package such as a printed circuit board or a ceramic circuit board ("IC package"). Generally, the flip-chip process entails disposing a plurality of raised and embedded contacts, e.g., in the form of solder balls or bumps, on the upper major surface of the chip or die (termed a ball grid array, "BGA"), wherein the solder balls or bumps may overlie and connect with internal vias of the IC device. The IC chip or die is then "flipped" over so that the solder balls or bumps face and are mated with a corresponding ball grid array (BGA) or bonding pads on the substrate surface, which BGA or bonding pads may also overlie and electrically contact internal vias of the substrate for electrically connecting underlying metallization levels, patterns, etc. Once mated, the solder bumps or balls of the IC die or chip and the corresponding solder bumps or balls or bonding pads of the substrate are heated to effect reflow and mutual bonding, whereby each solder ball or bump forms a bond between the chip or die and the substrate. As a consequence, each bonded combination functions as both an electrical and physical contact.

According to flip-chip methodology, electrically conductive balls or bumps comprising a solder material are formed on the IC chip or die, as well as on the mating surface of the substrate. Bonding between the two sets of solder balls or bumps is effected by application of heat to the chip or die and the substrate. The application of heat causes both sets of solder-based balls or bumps to reflow, thereby providing physical and ohmic connection therebetween, causing the mated pairs of solder-based wetted balls or bumps to at least partially collapse. Often, a "pancake" shape is created which advantageously reduces interconnection length and resistance.

Flip-chip contact arrangements, such as described above, are susceptible to exhibiting poor ohmic contact performance and/or poor physical bonding, in extreme instances leading to device failure. Poor ohmic resistance and/or poor physical bonding may result from a number of factors, including, inter alia, offset or misalignment of the solder ball or bump forming the external, raised contact, and the underlying internal via structure; presence of voids in the ball/via structure, whether arising during manufacture or subsequent thereto as a result of, e.g., electromigration of one or more metallic elements or components thereof; and layer separation, i.e., delamination, disbonding, or oxidation of the surfaces of e.g., the solder ball or bump and the underlying via due to compositional differences which result in poor mutual adhesion.

As a consequence of the above-described several possible, but distinct, scenarios or mechanisms leading to poor performance of BGA and flip-chip contact/via structures, inspection and/or failure analysis is generally necessary for determining the particular mechanism responsible for poor performance or failure of a particular device or component. However, methodology for performing simple, reliable, and rapid sample preparation for visual or X-ray failure analysis and/or inspection of a particular area-of-interest (AOI) of a BGA or flip-chip array with associated underlying vias is presently unavailable. Moreover, a convenient method for performing high magnification, visual and/or X-ray inspection and/or analysis of an AOI of a BGA or flip-chip array of either or both of a semiconductor IC chip or die and circuit board or IC package therefor, is similarly presently unavailable.

Accordingly, there exists a need for improved methodology for simple, reliable, and rapid X-ray inspection and/or analysis of solder ball/underlying via structures of a particular AOI of a semiconductor IC chip or die or circuit board therefor, which methodology is capable of revealing all pertinent internal structural features e.g., flip-chip devices and contacts, and does not require costly, specialized, or customized equipment or apparatus.

The present invention, wherein a particular AOI of a BGA or flip-chip array of solder ball contacts/underlying vias of an IC die or chip or circuit board therefor is isolated and removed therefrom and mounted on a transparent substrate, which in turn is held by a rotatable gripping means, e.g., a rotatable and tiltable chuck, thereby facilitating performing visual and/or X-ray transmission inspection and/or analysis at high magnification levels, effectively addresses the need for improved methodology for performing failure analysis leading to development of improved, low ohmic resistance, well-aligned, void-free, adherent ball contact/underlying via structures. Further, the means and methodology provided by the present invention enjoy diverse utility in the manufacture of numerous and various types of electrical and electronic devices and/or components utilizing ball contact/via combinations.

DISCLOSURE OF THE INVENTION

An advantage of the present invention is an improved method for simple, reliable, and rapid, X-ray radiography inspection and/or analysis at high magnification of raised ball contact/underlying via combinations or structures of electrical components.

Another advantage is an improved method for performing high magnification, X-ray analysis of BGA or flip-chip raised contact/underlying via structures of particular AOI's of semiconductor IC devices and/or printed circuit board or ceramic circuit board.

Additional advantages and other features of the present invention will be set forth in the description which follows and in part will become apparent to those having ordinary skill in the art upon examination of the following or may be learned from the practice of the present invention. The advantages of the present invention may be realized as particularly pointed out in the appended claims.

According to one aspect of the present invention, the foregoing and other advantages are obtained in part by a method for performing inspection and/or analysis of raised and embedded electrical contacts and associated underlying vias of an electrical component having opposing first and second major surfaces, the first major surface including an array of closely spaced-apart raised electrical contacts with respective underlying vias.

Within an electrical component, an area-of- interest ("AOI") comprising a row of contacts on said first major surface and respective underlying vias is identified. The AOI, including at least one of the raised electrical contacts with its respective underlying via, is isolated for X-ray imaging. X-ray images of the AOI are created, depicting at least one of the raised and embedded electrical contacts with its respective underlying via, and distinguishing at least one of the raised and embedded electrical contacts with its respective underlying via enabling a clear view for inspection and/or analysis of at least one of the raised and embedded electrical contacts and its respective underlying via.

According to embodiments of the present invention, an electrical component comprises a semiconductor integrated circuit ("IC") device package or a printed circuit board ("PCB") or ceramic circuit board ("CCB") having a two-dimensional, row-and-column, grid-shaped array of raised, ball grid array ("BGA") or flip-chip contacts on the first major surface thereof, wherein adjacent rows and columns of the two-dimensional, grid-shaped arrays of raised contacts are spaced apart from about 200 to about 600 $\mu$m.

According to embodiments of the present invention, identifying an AOI comprises selecting at least one row or column of contacts of the two-dimensional, grid-shaped array of contacts as the AOI; and isolating the AOI comprises separating each selected row or column of contacts from the electrical or electronic device or component. Isolating can also be performed in non-physical manners such as electronically, e.g., using computed tomography imaging (CT scan), or other manners that allow unobstructed X-ray images of the AOI to be made.

In certain embodiments of the present invention, the separated AOI is mounted on an X-ray transparent substrate; and X-ray images of each separated row or column of contacts and the underlying vias are created. The X-ray images are utilized to inspect and/or analyze the AOI.

According to particular embodiments of the present invention, creating X-ray images comprises performing X-ray radiography transmission inspection, or other form of X-ray inspection such as a reflective X-ray arrangement, for example, and/or analysis of the AOI, including positioning an X-ray source and an X-ray detector facing opposite surfaces of the separated row or column. In certain embodiments, a separated row or column is mounted on an X-ray transparent substrate surface such that the vias are substantially parallel to the substrate surface. In certain other embodiments, the X-ray source is positioned adjacent to and facing the separated row or column and the X-ray detector is positioned beneath the substrate, facing the separated row or column.

According to other embodiments of the present invention, mounting the AOI for X-ray imaging includes installing the X-ray transparent substrate with the separated row or column mounted thereon in a rotatable, tiltable chuck or mount, the separated row or column being mounted on a glass or polymer-based substrate; and the mounting is accomplished by a transparent adhesive or double-sided transparent adhesive tape.

According to another aspect of the present invention, a method for performing inspection and/or analysis of raised electrical contacts and respective underlying vias of electrical devices and/or components comprises the sequential steps of:

(a) providing an electrical or electronic device or component having opposing first and second major surfaces, the first major surface including an array of closely spaced-apart raised electrical contacts with respective underlying vias, wherein the electrical device or component is a semiconductor integrated circuit ("IC") device package or a printed circuit board ("PCB") or ceramic circuit board ("CCB") having a two-dimensional, row-and-column, grid-shaped array of raised, ball-grid array ("BGA") or flip-chip contacts on the first major surface thereof;

(b) isolating an area-of-interest ("AOI") of the first major surface, the AOI comprising at least a portion of at least one of the rows and columns forming the grid-shaped array of contacts; and (c) performing X-ray inspection and/or analysis of at least one raised contact with respective underlying via of the AOI for determining presence of any misalignment, voids, and delaminations.

According to embodiments of the invention, adjacent rows and columns of the two-dimensional, grid-shaped arrays of raised contacts are spaced apart from about 200 to about 600 $\mu$m.

According to further embodiments of the present invention, X-ray inspection comprises performing X-ray radiography transmission inspection, or other form of X-ray inspection such as a reflective X-ray arrangement, for example, and/or analysis of the AOI, including positioning an X-ray source and an X-ray detector so as to face opposite surfaces of the AOI. In certain embodiments, the AOI is mounted on the surface of the X-ray transparent substrate such that the vias within the AOI are substantially parallel to the substrate surface. In certain embodiments, the X-ray source is positioned adjacent to and facing the AOI, and the X-ray detector is positioned beneath the substrate, facing the AOI, wherein installation of an X-ray transparent substrate with the AOI mounted thereon is in a rotatable, tiltable chuck or mount permitting three-dimensional images of the AOI to be created.

Additional advantages and aspects of the present invention will become apparent to those skilled in the art from the following detailed description, wherein embodiments of the present invention are shown and described, simply by way of illustration of the best mode contemplated for practicing the present invention. As will be described, the present invention is capable of other and different embodiments, and its several details are susceptible of modification in various obvious respects, all without departing from the spirit of the present invention. Accordingly, the drawings and description are to be regarded as illustrative in nature, and not limitative.

BRIEF DESCRIPTION OF THE DRAWINGS

The following detailed description of the embodiments of the present invention can best be understood when read in conjunction with the following drawing, in which the various features are not drawn to scale but rather are drawn as to best illustrate the pertinent features, and in which like reference numerals are employed throughout to designate similar features, wherein.

DESCRIPTION OF THE INVENTION

Figure 2:
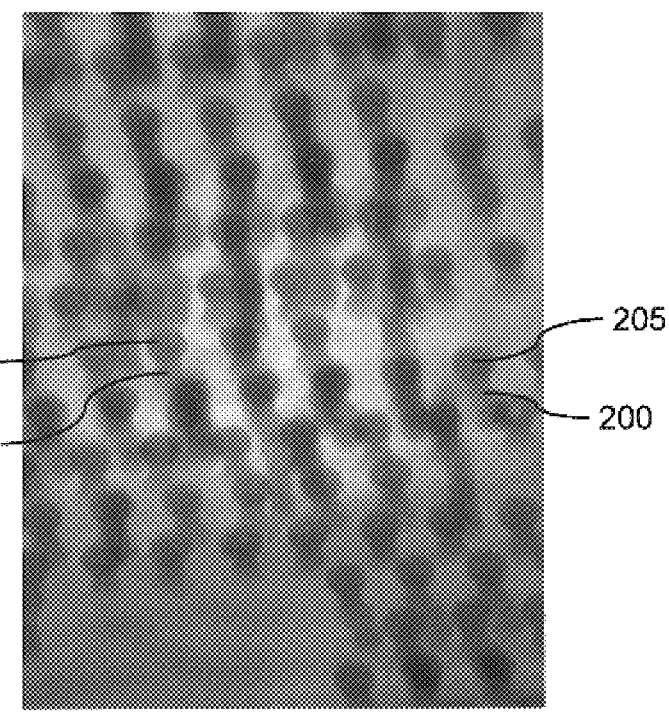
FIG. 2 depicts a prior art image exhibiting a cluttered field of view of many via rows in an organic package substrate.
Figure 3:
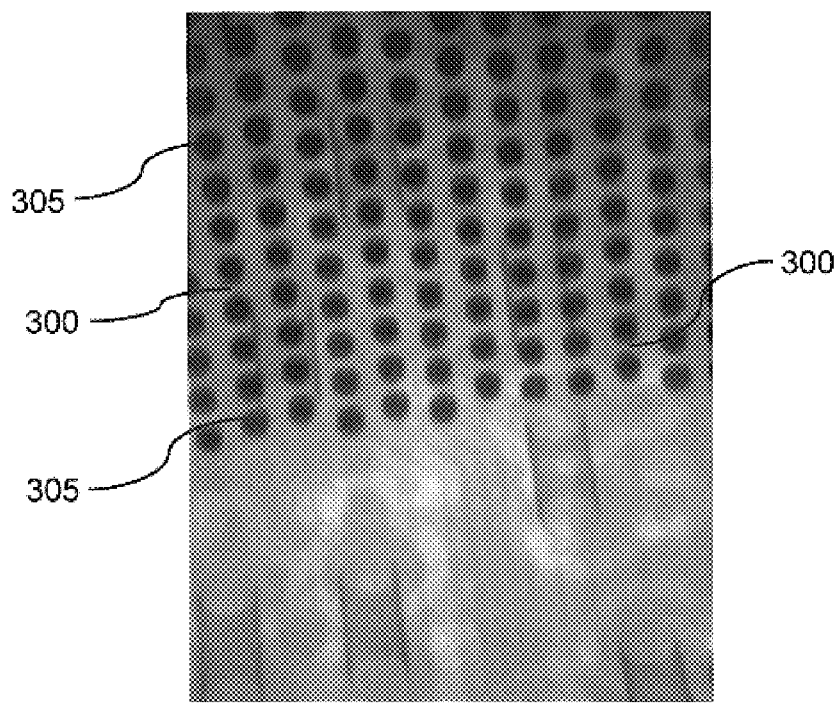
FIG. 3 depicts a prior art image exhibiting a cluttered field of view of many via rows in a ceramic package substrate.

Current X-ray imaging techniques of electrical components capture multiple rows of vias in each image. This leads to unclear and cluttered images that are difficult to analyze because of the inclusion of vias that are not being inspected, for example FIGS. 2 and 3. In such images it is difficult to distinguish features and defects in the vias that are being inspected and/or analyzed. The problem of cluttered, unclear images is especially compounded when attempts are made at creating three-dimensional images of the vias under inspection. FIG. 2 depicts the clutter and confusion present in current X-ray images of vias 200 and contacts 205 in an organic package substrate where the image is an oblique view of the package. FIG. 3 depicts the clutter and confusion present in current X-ray images of vias 300, mostly obscured by the ball grid array, composed of contacts 305, in a ceramic package substrate where the image is an oblique view of the package.

Figure 7:
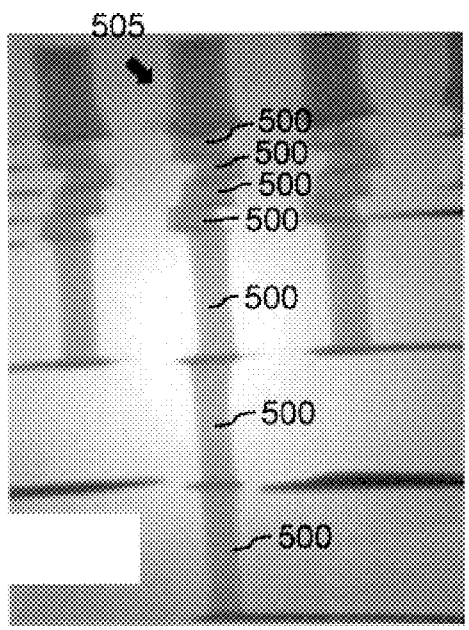
FIG. 7 depicts a side view, two-dimensional image of a row of contacts and their respective underlying vias made according to the method of the present invention without other vias cluttering the field of view.

The present invention is based upon the discovery that X-ray imaging inspection and/or analysis of raised contact/underlying via structures and combinations, such as BGA and/or flip-chip contact arrays utilized in electrical and electronic devices and components, can be readily performed at high magnification, and without interference or clutter from extraneous structures. By selecting an area-of-interest (AOI) from the array of contacts, isolating the AOI, as by cutting for example, to form a narrow, elongated strip which is easily mounted on a transparent substrate, thereby permitting close positioning of the radiation source to the AOI and affording very high magnification levels, examination of the internal structure of the raised contact/internal via combination is possible utilizing a clear, unobstructed X-ray image of the selected electrical contacts and respective underlying vias. An exemplary X-ray image made according to the present invention is depicted in FIG. 7. In addition, a small sample size facilitates mounting of the transparent substrate with the AOI thereon in a rotatable chuck of e.g., an X-ray apparatus, thereby enabling advantageous variation of the viewing angle.

Figure 1A:
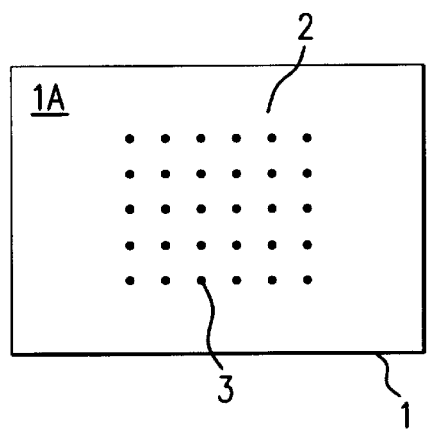
FIGS. 1(A)–1(F) schematically illustrate successive steps for a method of separating a row of contacts and their respective underlying vias from an electrical or electronic device or component.

Referring now to FIG. 1, and with particular reference to FIG. 1(A), in a first step according to the invention, there is provided a semiconductor integrated circuit (IC) device package or printed circuit board ("PCB") or ceramic circuit board ("CCB") therefor (designated in each case by reference numeral 1), having a two-dimensional, row-and-column array 2 of raised, ball-grid array ("BGA") or flip-chip contacts 3 on a portion of a first major surface 1A thereof. At least some of the raised contacts 3 of array 2 overlie internal vias (not shown in the drawing) of the IC device package or circuit board 1 for electrical contact to a semiconductor IC chip or die therein or to underlying metallization level(s) of the circuit board. The raised solder balls or bumps of array 2 typically have diameters in the range of from about 100 to about 200 $\mu$m, and adjacent rows and columns of the two-dimensional array 2 are spaced apart from about 200 to about 600 $\mu$m, e.g., about 400 $\mu$m.

Figure 1B:
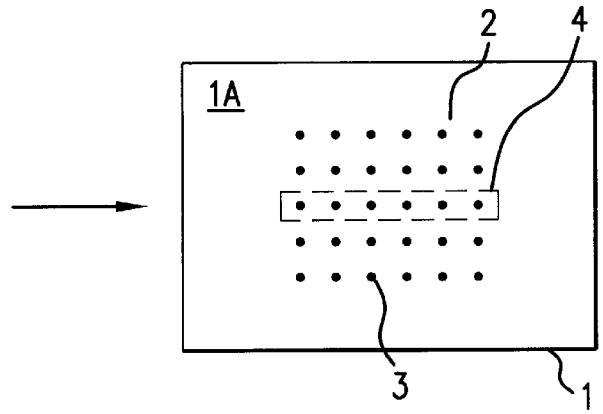

Referring now to FIG. 1(B), in the next step according to the inventive methodology, a particular area-of-interest ("AOI") 4 of array 2 is selected for inspection and/or analysis, based upon, for example, the nature of device failure or measurement of an electrical or other property indicating, e.g., poor ohmic contact in a particular area or raised contact/underlying via combination. AOI 4 may comprise at least a portion of one or more columns and/or rows of array 2 of raised contacts with respective underlying vias. By way of illustration, but not limitation, AOI 4 may comprise a single horizontally-oriented row of raised contacts/underlying via structures, as in the illustrated embodiment.

Figure 1C:
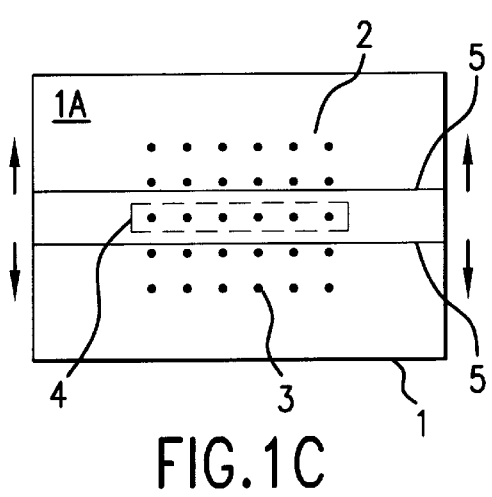
Figure 1D:
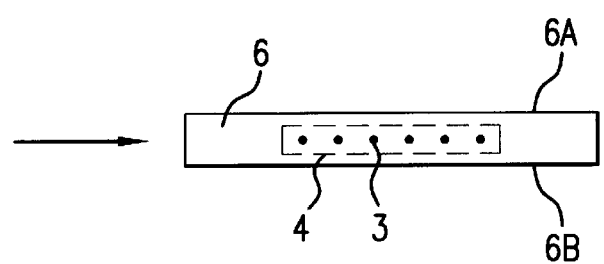
Figure 1E:
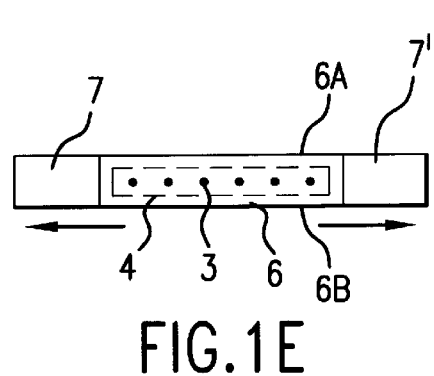

The AOI 4 is then isolated for inspection. In certain embodiments of the invention, the isolation involves removing the row from the IC device package or circuit board. For example, as shown in FIG. 1(C), AOI 4 is separated from array 2 by cutting, as by use of a wire saw having a silicon or diamond blade or slurry, along parallel lines 5, 5' extending along the spaces between the selected row and the neighboring rows on both sides of the selected row, to form the narrow, elongated strip 6 shown in FIG. 1(D) and having opposed cut surfaces 6A, 6B. By way of example only, if adjacent rows of the array 2 are spaced apart by about 400 $\mu$m, cutting along lines 5, 5' with a conventional wire saw yields a narrow strip having a width between opposed cut surfaces 6A, 6B of from about 10 to about 15 mils, depending upon the kerf loss.

Isolation of the AOI 4 is accomplished in different manners in other embodiments of the invention. For example, instead of a wire saw, laser cutting of the AOI 4 may be employed. Further, alternate embodiments may include other ways of isolating the AOI 4, including differentiating the AOI 4 so that it appears differently from the rest of the package in an X-ray image. This differentiation avoids the need to separate the AOI 4 from the package. Performing a CT scan on the AOI is yet an alternative manner to distinguish the AOI from the rest of the integrated circuit.

Optionally, unwanted portions 7, 7' of strip 6, when cutting is utilized to isolate the AOI, outside AOI 4 are trimmed from either or both ends thereof, by any convenient means, e.g., a wire saw.

Figure 1F:
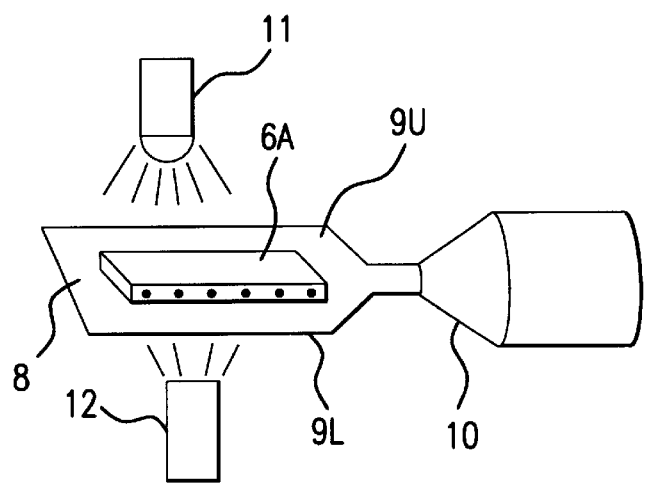

Referring now to FIG. 1(F), in the next step of the inventive methodology, the separated row including AOI 4 is mounted, via a transparent adhesive or double-sided transparent adhesive tape, to an elongated transparent substrate 8 having a flat planar mounting, or upper surface 9U, e.g., of glass or polymer-based material, one end of substrate 8 being secured for rotation about a longitudinally extending axis, e.g., by a chuck 10 of an X-ray or visual measurement/analysis apparatus.

According to an embodiment of the present invention, the separated row is secured to upper surface 9U of substrate 8 such that the vias are substantially parallel to upper surface 9U, for example by a clear adhesive, and an X-ray or visual light source 11 is positioned above and closely adjacent the separated row, and an X-ray or other type radiation detector 12 is positioned beneath the lower surface 9L of substrate 8. Such arrangement facilitates obtaining, for example, high magnification, X-ray transmission images of the raised solder balls or bumps and their respective underlying internal vias, whereby the presence of any offsets or misalignments, voids, and layer separations (delaminations) are readily observable. The rotatable chuck 10 allows for performing X-ray transmission imaging at multiple viewing angles of the AOI 4 and the close positioning of the subject strip to the X-ray source 11 permits obtainment of well-defined images at high magnification, e.g., from about 500 to about 1000 times magnification.

Figure 4:
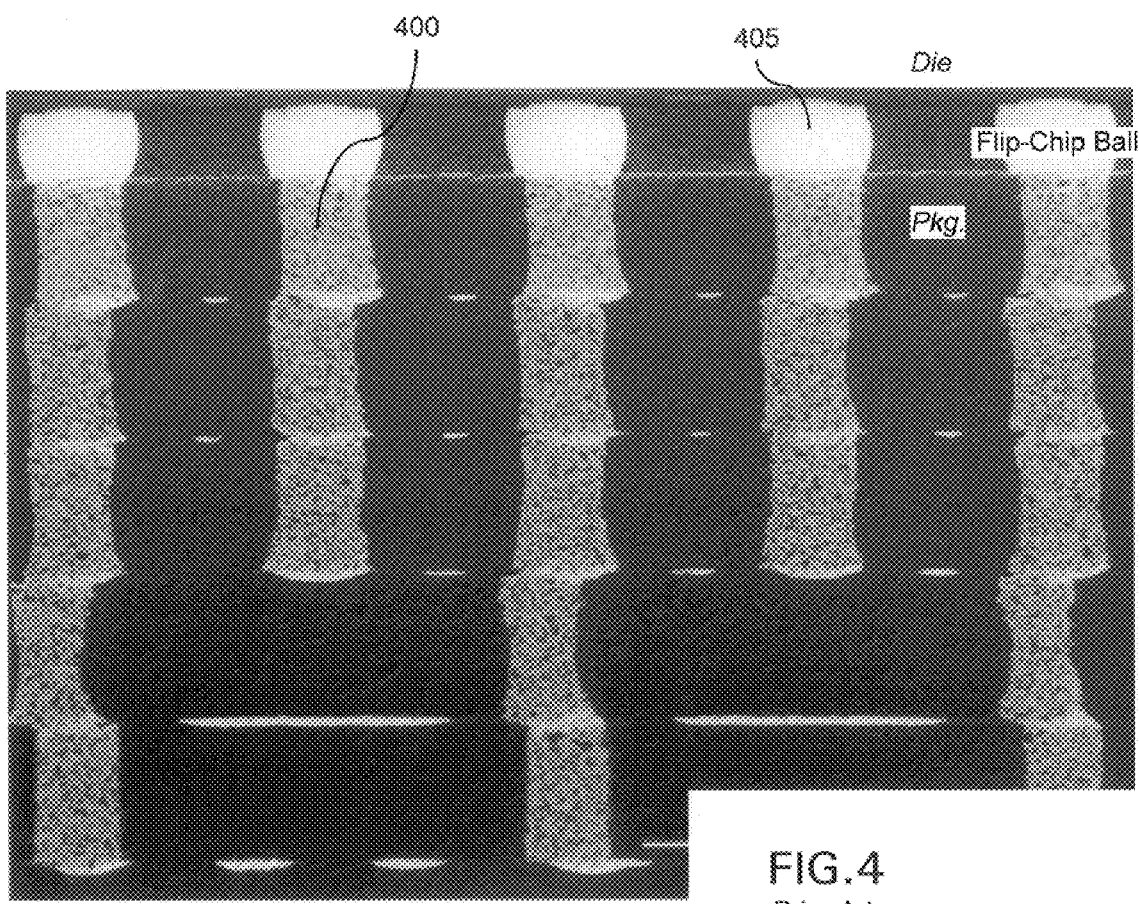
FIG. 4 depicts a prior art, two-dimensional image of contacts and their respective underlying vias.
Figure 6:
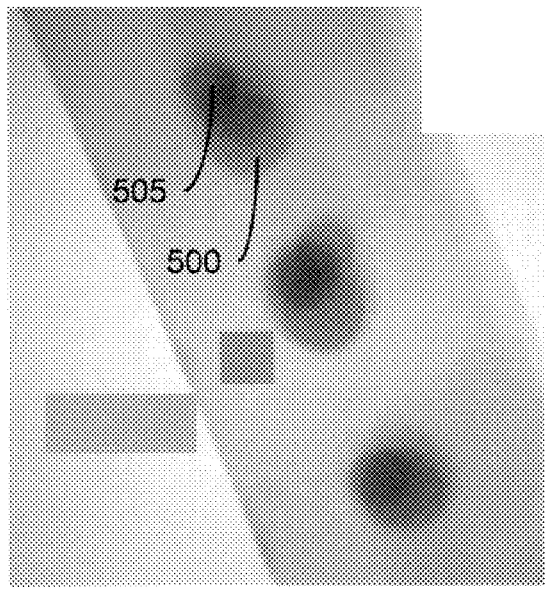
FIG. 6 depicts a magnified, three-dimensional, top view of the row of contacts and their respective underlying vias depicted in FIG. 5.

X-ray images of the AOI are made in order to create two-dimensional side view images of the vias. An example of such an image is depicted in FIG. 7. Note the clarity with which the vias 500 and the contacts 505 are seen as compared with the prior art image depicted in FIG. 4, where the image of vias 400 is granular, and the image of the contacts 405 is washed-out. Such clear images, as depicted in FIGS. 6 and 7, allow inspection of the contacts 505 and their respective underlying vias 500 for misalignment, as well as inspection of the internal structure of the vias 500 for defects such as voids, cracks and depleted metal, and delaminations. Multiple two-dimensional images are utilized to render three-dimensional data about the vias. Such three-dimensional data allow creation of three-dimensional images of the contacts and their respective underlying vias.

Figure 5:
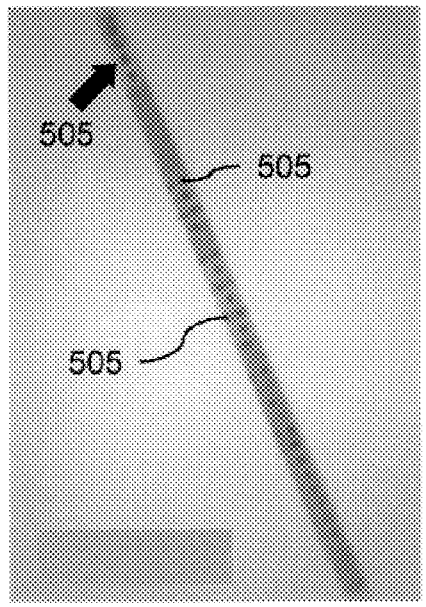
FIG. 5 depicts a top view, two-dimensional image of a row of contacts and their respective underlying vias made according to the method of the present invention without other vias cluttering the field of view.
Figure 8:
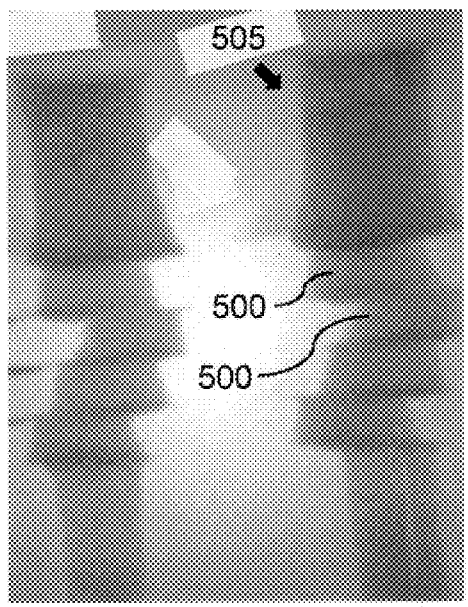
FIG. 8 depicts a magnified side view of the area of interest depicted in FIG. 7.
Figure 9:
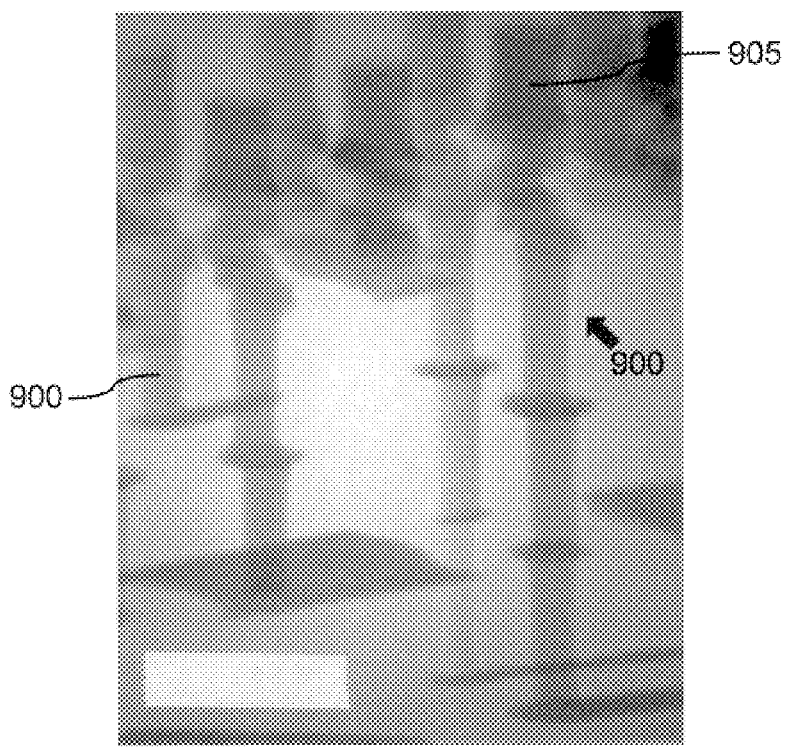
FIG. 9 depicts an oblique view, three-dimensional image of two rows of contacts and their respective underlying vias made according to the method of the present invention without other vias cluttering the field of view.
Figure 10:
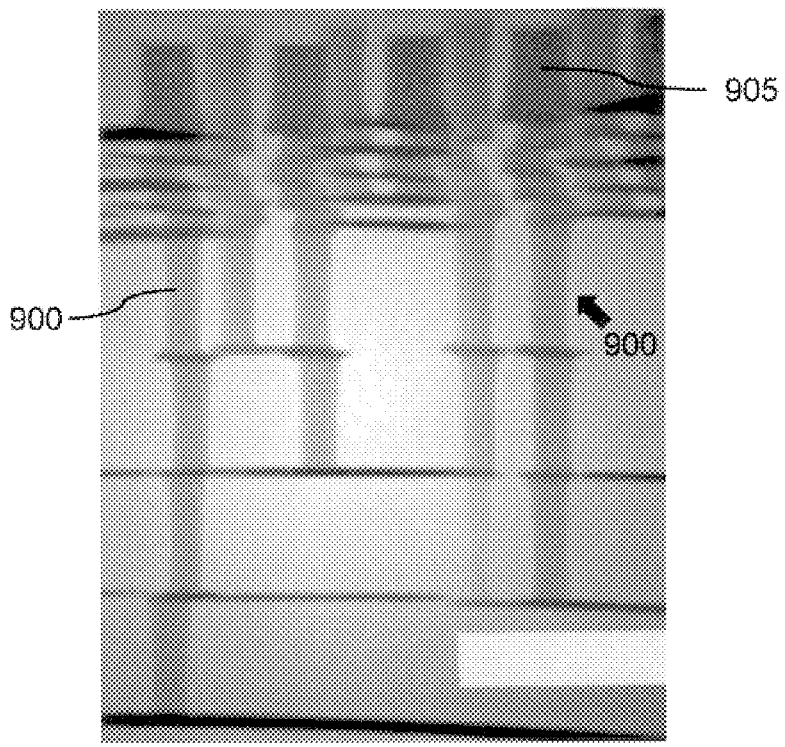
FIG. 10 depicts a side view, three-dimensional image of two rows of contacts and their respective underlying vias made according to the method of the present invention without other vias cluttering the field of view.

Defects such as voids, cracks and depleted metal, and delamination are easier to discover utilizing three-dimensional images of the contacts and their respective underlying vias. FIGS. 5, 7, and 8 depict two-dimensional images of contacts 505 and their respective underlying vias 500 made according to the present invention, and demonstrate the clarity and ease of inspecting contacts 505 and their respective underlying vias 500 that the present invention provides. Accordingly, the AOI is tilted at various angles, and stereo pair imaging is utilized, so that X-ray images are three-dimensional of the contacts and their respective underlying vias, as depicted in FIGS. 9 and 10. Because there are only a few rows of vias 900 contained within the AOI, or the AOI has been sufficiently differentiated from the remainder of the integrated circuit, three-dimensional images of the contacts 905 and their respective underlying vias 900 are free from background clutter and are not obscured by images of vias not intended to be inspected. Lack of clutter and clear images makes identification of defects between the contacts 905 and their respective underlying vias 900, as well as defects contained within vias 900, much more feasible. For example, the two rows of vias 900 depicted in FIGS. 9 and 10 are more easily seen, show more detail, and are capable of being displayed at higher magnification while retaining clarity than the multiple rows of vias 200 and 300, respectively depicted in FIGS. 2 and 3, are.

A number of advantages are thus provided by the inventive methodology, including, inter alia, simple, rapid, reliable, X-ray imaging which effectively removes clutter, i.e., extraneous matter, from the subject field or area-of-interest (AOI). Moreover, the inventive X-ray imaging method involving isolation of the selected AOI, permits close positioning of an X-ray or other type radiation source to the subject, thereby facilitating obtainment of well-defined X-ray or other type transmission images at high magnification. In addition, the inventive methodology is conveniently performed without incurring significant additional expense. Finally, the present invention is not limited to use with semiconductor IC device packages and circuit boards therefor, but rather is applicable to performing rapid, reliable inspection and/or analysis of all manner of electrical devices and/or components having raised contact/underlying via or via-type structures.

In the previous description, numerous specific details have been set forth, such as specific materials, structures, processes, etc., in order to provide a better understanding of the present invention. However, the present invention can be practiced without resorting to the details specifically set forth. In other instances, well-known processing techniques and structures have not been described in detail in order not to unnecessarily obscure the present invention.

Only the preferred embodiments of the present invention and but a few examples of its versatility are shown and described in the present invention. It is to be understood that the present invention is capable of use in various other combinations and environments and is susceptible of changes and/or modifications within the scope of the inventive concept as expressed herein.

What is claimed is:

1. A method for inspecting contacts and underlying vias of an electrical component, comprising the steps of:
   identifying a row of contacts and respective underlying vias for inspection;
   isolating the identified row from other rows of the electrical component by physically separating the identified row from the electrical component;
   creating images of the contacts and respective underlying vias utilizing X-ray techniques; and
   inspecting the X-ray images of the contacts and respective underlying vias.

2. The method of claim 1, wherein creating images of the contacts and respective underlying vias utilizing X-ray techniques further comprises:
   positioning the X-ray equipment such that the created images are magnified.

3. The method of claim 1, wherein creating images of the contacts and respective underlying vias utilizing X-ray techniques comprises:
   aligning X-ray equipment with the identified row such that two-dimensional images of the contacts and respective underlying vias are created.

4. The method of claim 3, wherein:
   the two-dimensional images of the contacts and respective underlying vias are used to render three-dimensional data about the contacts and respective underlying vias.

5. The method of claim 3, wherein inspecting comprises:
   determining the presence of misalignment, voids, cracks, and delaminations.

6. The method of claim 3, wherein creating images of the contacts and respective underlying vias utilizing X-ray techniques further comprises:

provisioning the X-ray equipment such that the created images are magnified.

7. The method of claim 1, wherein creating images of the contacts and respective underlying vias utilizing X-ray techniques comprises:

aligning X-ray equipment with the identified row such that three-dimensional data about the contacts and respective underlying vias are created; and utilizing the three-dimensional data to create three-dimensional images of the contacts and respective underlying vias.

8. The method of claim 7, wherein inspecting comprises:

determining the presence of misalignment, voids, and delaminations.

9. The method of claim 7, wherein creating images of the contacts and respective underlying vias utilizing X-ray techniques further comprises:

positioning the X-ray equipment such that the created images are magnified.

10. The method of claim 1, wherein creating images of the contacts and respective underlying vias utilizing X-ray techniques comprises:

aligning X-ray equipment with the identified row such that stereo pair images of the contacts and respective underlying vias are created, wherein the stereo pair images are utilized to create three-dimensional images of the contacts and respective underlying vias.

11. The method of claim 1, wherein physically separating the row includes sawing the identified row from the electrical component.

12. The method of claim 1, wherein physically separating the identified row includes laser cutting the identified row from the electrical component.

* * * * *